(12) United States Patent
Lee et al.

(10) Patent No.: US 10,190,971 B2
(45) Date of Patent: Jan. 29, 2019

(54) ANALYZING COLOR OF COLOR ALLOY USING REFLECTANCE

(71) Applicant: KOREA INSTITUTE OF INDUSTRIAL TECHNOLOGY, Cheonan-si, Chungcheongnam-do (KR)

(72) Inventors: Hyo Soo Lee, Incheon (KR); Hyouk Chon Kwon, Seoul (KR); Hai Joong Lee, Incheon (KR); Heong Won Shin, Incheon (KR)

(73) Assignee: Korea Institute of Industrial Technology, Cheonan-si, Chungcheongnam-do (KR)

( * ) Notice: Subject to any disclaimer, the term of this patent is extended or adjusted under 35 U.S.C. 154(b) by 0 days.

(21) Appl. No.: 15/529,713

(22) PCT Filed: Nov. 11, 2015

(86) PCT No.: PCT/KR2015/012135
§ 371 (c)(1),
(2) Date: May 25, 2017

(87) PCT Pub. No.: WO2016/085164
PCT Pub. Date: Jun. 2, 2016

(65) Prior Publication Data
US 2017/0328831 A1 Nov. 16, 2017

(30) Foreign Application Priority Data
Nov. 28, 2014 (KR) .......................... 10-2014-0168578

(51) Int. Cl.
*G01J 3/46* (2006.01)
*G01N 21/25* (2006.01)
(Continued)

(52) U.S. Cl.
CPC ............... *G01N 21/25* (2013.01); *G01J 3/00* (2013.01); *G01J 3/46* (2013.01); *G01N 21/64* (2013.01); *G01N 21/65* (2013.01); *G01N 33/20* (2013.01)

(58) Field of Classification Search
CPC ........ G01J 3/28; G01J 3/00; G01J 3/46; G01J 3/02; G01N 21/65; G01N 21/64; G01N 21/25; G01N 33/20
See application file for complete search history.

(56) References Cited

U.S. PATENT DOCUMENTS

2009/0086192 A1* 4/2009 He ........................ G01J 1/124
356/73

FOREIGN PATENT DOCUMENTS

JP         09-145597 A      6/1997
KR    10-2000-0077034 A    12/2000
(Continued)

OTHER PUBLICATIONS

PCT/KR2015/012135—International Search Report dated Mar. 28, 2016, 2 pages.
(Continued)

*Primary Examiner* — Abdullahi Nur
(74) *Attorney, Agent, or Firm* — Rabin & Berdo, P.C.

(57) ABSTRACT

The present invention relates to a method for analyzing the color of a color alloy and, more particularly, to a method for analyzing the color of a color alloy wherein, on the basis of the fact that a different color appears according to the composition of an alloy, the wavelength-wise reflectance related to a color, which is held according to each alloy composition, and that related to a color, which is held by a measurement object that is to be measured, are compared, thereby determining the color held by the measurement object.

17 Claims, 6 Drawing Sheets

(51) Int. Cl.
*G01N 21/64* (2006.01)
*G01J 3/00* (2006.01)
*G01N 21/65* (2006.01)
*G01N 33/20* (2006.01)

(56) References Cited

FOREIGN PATENT DOCUMENTS

KR       10-0803973 B1     2/2008
KR   10-2014-0146645 A   12/2014

OTHER PUBLICATIONS

Yang, Ji Hun et al., "Color Investigation of Ti Composites Synthesized by Magnetron Sputtering Technique," RIST Journal of R&D, vol. 21, No. 2, Jun. 30, 2007, pp. 88-92.

* cited by examiner

ANALYZING COLOR OF COLOR ALLOY USING REFLECTANCE

BACKGROUND OF THE INVENTION

Field of the Invention

The present invention relates to a method for analyzing the color of a color alloy using reflectance and, more specifically, to a method for quantitatively analyzing the color held by a color alloy using the data obtained from the emitted light after emitting light to the color alloy, based on the fact that a different color appears according to the composition of an alloy.

Related Art

The conventionally-used terms, color and chromaticity, refer to "a color in a broad sense" and are expressed by classifying into three attributes of value, hue, and saturation.

The concept for each of the three attributes may be explained as follows. The "value" refers to brightness and becomes a reference to distinguish the presence of a color. For example, value represents the degree of brightness of white, gray, and black series.

The "hue" represents a color in a narrow sense and is a reference to distinguish red, yellow, green, blue, etc., and it is possible to have the same value although there is a difference in hue.

Lastly, the "saturation" refers to clearness of a color, for example, if red series are classified according to saturation, they may be classified into pink, light red, medium red, dark red, etc.

The present invention relates to a method for determining the composition of an alloy by measuring the unique wavelength-wise reflectance possessed by each alloy, using the hue recognition characteristics of metals having their unique hues, followed by comparing with the hue actually possessed by the alloy, thereby obtaining the data with regard to the hue held by the alloy.

In a case when the physical properties necessary for an alloy composition required in the industry and the subsequent data relating to a color of the alloy are available, the present invention enables the designing of an alloy using the composition-wise data according to the hue suggested by the present invention.

A previous method for determining the hue of an alloy was to use a reference, "Pantone book", well-known in the design field. The Pantone book assigns a unique number for each color and simultaneously provides the corresponding color according to the Pantone color number.

The Pantone book refers to a print manufactured by Pantone LLC (USA) and a color atlas manufactured by color matching of inks according to materials. The number of colors disclosed in the Pantone book consist of 1015 coated colors and 1013 uncoated colors. As the marks indicated in the Pantone, "c" (which is an abbreviation for coated) is to be added to the rear part of the color chart and "u" (which is an abbreviation for uncoated) is to be added to the rear part of the color chart for the uncoated.

FIG. 1 shows images according to the hue of the Pantone book by the conventional technology.

Referring to FIG. 1, the code mark for the coated color is indicated as Pantone 421C and the code mark for the uncoated color is indicated as Pantone 421U. Currently, the Pantone colors are released in various forms for printing, textiles, plastics, webs, etc.

Conventionally, with respect to the Pantone colors, colors were determined by a method of comparing the colors of alloys and by the naked eye, and thus it was not possible to perform a quantitative analysis.

Korean Patent No. 10-803973 relates to a method for predicting the composition of a Cu alloy and, more specifically, to a method for calculating the composition of a Cu alloy by the measurement of a color using the hue recognition characteristics of metals.

In predicting the composition of a Cu alloy, a method which includes measuring the hue of a Cu alloy and calculating the composition of the Cu alloy by substituting the measured hue into a particular equation, in which when the added atom is Zn, the equation used for measurement is Equation 1 below; when the added atom is Sn, the equation used for measurement is Equation 2; and in a case of a Cu—Al alloy when the added atom is Al, the equation used for measurement is Equation 3, was used.

$$\text{hue } 1 = 63.59 - 25.99 e^{(-X1/19.78)} \quad \text{[Equation 1]}$$

$$\text{hue } 2 = 87.52 - 49.90 e^{(-X2/20.03)} \quad \text{[Equation 2]}$$

$$\text{hue } 3 = 102.52 - 64.98 e^{(-X3/7.149)} \quad \text{[Equation 3]}$$

In Equations 1 to 3, X1 represents the wt % of Zn, X2 represents the wt % of Sn, and X3 represents the wt % of Al.

In particular, it is described that the atoms to be added in Equations 1 to 3 are preferably in an amount of 25 wt % or less. The above patent document (Korean Patent No. 10-803973) employs the principle that the composition of an alloy is predicted by measuring the hue of an alloy using the hue recognition characteristics of metals having their unique hues. For the application of the principle described above, the above patent document discloses that a mathematical model for predicting composition for each of Cu alloys can be drawn by reading the color region of materials of various alloys of Cu—Zn, Cu—Sn, and Cu—Al by hue/saturation/value (HSV) data using the images coming from a 3 charge coupled device (CCD) color camera; databasing the result of reading; and performing the overall analysis of only the change in hue value among the results of reading, and provided.

However, although a data analysis on hue can be performed using the device described above, there was a problem in that the amount of the added atom is limited to be 25% and that an accurate quantitative analysis cannot be performed by presetting the image state of the CCD camera alone.

PRIOR ART DOCUMENT

Patent Document (Patent Document 0001) Korean Patent No. 10-803973

SUMMARY OF THE INVENTION

The present invention has been made in an effort to solve the above problems, and an object of the present invention is to provide a method for quantitatively analyzing a sample alloy using the data photographed by a spectrophotometer with respect to coated color and uncoated color disclosed in the Pantone book by having the data imaged in the Pantone book as the basic database.

Additionally, another object of the present invention is to provide a method for designing an alloy which can provide an alloy that meets the request of consumers.

In order to achieve the above objects, the present invention provides a method for analyzing the color of a color alloy using reflectance, in which the method for analyzing the color of a color alloy includes: charging a measurement object and a reference object into a sample charging unit of a spectrophotometer; emitting light to a reference object and to a measurement object, using a light source of the spectrophotometer, and reflecting the same; measuring the wavelength-wise reflectance while changing the wavelength of the light, which is directed from the light source to the measurement object and to the reference object, by a detection unit of the spectrophotometer; calculating the absolute value of the difference between the measured wavelength-wise reflectance of the measurement object and of the reference object, as the deviation value, and calculating the average value thereof, in an operation unit; dividing the average value by the reflectance value of the reference object, thereby obtaining the mean deviation ratio of reflectance; and comparing the average deviation ratio with a preset reference value, thereby determining whether the colors are the same or not by an operation unit, wherein, in determining whether the colors are the same or not by an operation unit, when the value of the mean deviation ratio is less than the preset reference value the colors are determined to be the same by the operation unit, whereas when the value of the mean deviation ratio is equal to or higher than the preset reference value the colors are determined not to be the same by the operation unit. The method for analyzing the color of a color alloy with such a feature can quantitatively measure the wavelength-wise reflectance according to the composition of an alloy using a spectrophotometer instead of relying on the naked eye of humans, and also provides an effect of an automated analysis method for analyzing colors using a recording medium, in which the information on the composition of the alloy, wavelength-wise reflectance, and the color of the alloy are included therein.

Advantageous Effects of the Invention

According to a method for analyzing the color of a color alloy according to the present invention, the wavelength-wise reflectance according to the composition of an alloy can be quantitatively measured using a spectrophotometer instead of relying on the naked eye of humans.

According to the method for analyzing the color of a color alloy of the present invention, an automated analysis method for analyzing colors using a recording medium, in which the information on the composition of the alloy, wavelength-wise reflectance, and the color of the alloy are included therein, can be provided.

According to a method for analyzing the color of a color alloy of the present invention, a database with regard to the color and composition of an alloy can be established using a spectrophotometer.

According to a method for designing a color alloy of the present invention, the reflectance can be measured using a recording medium inserted into an electronic operation device and the composition of an alloy can be predicted.

DESCRIPTION OF EXEMPLARY EMBODIMENTS

Figure 1:
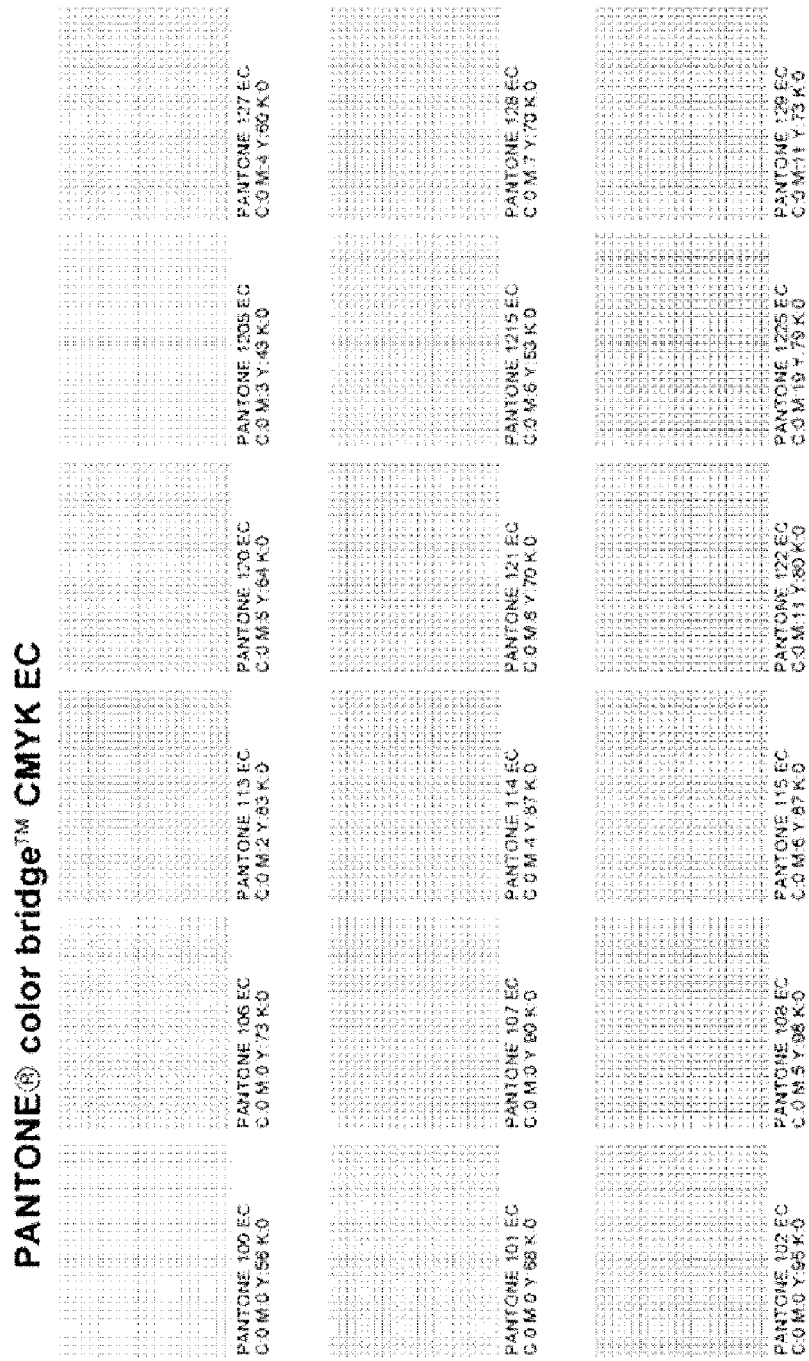
FIG. 1 shows images according to the hue of the Pantone book by the conventional technology.

The present invention provides a method for analyzing the color of a color alloy using reflectance, wherein the method for analyzing the color of a color alloy includes: charging a measurement object and a reference object into a sample charging unit of a spectrophotometer; emitting light to a reference object and to a measurement object, using a light source of the spectrophotometer, and reflecting the same; measuring the wavelength-wise reflectance while changing the wavelength of the light, which is directed from the light source to the measurement object and to the reference object, by a detection unit of the spectrophotometer; calculating the absolute value of the difference between the measured wavelength-wise reflectance of the measurement object and of the reference object, as the deviation value, and calculating the average value thereof, in an operation unit; dividing the average value by the reflectance value of the reference object, thereby obtaining the mean deviation ratio of reflectance; and comparing the average deviation ratio with a preset reference value, thereby determining whether the colors are the same or not by an operation unit, wherein, in determining whether the colors are the same or not by an operation unit, when the value of the mean deviation ratio is less than the preset reference value the colors are determined to be the same by the operation unit, whereas when the value of the mean deviation ratio is equal to or higher than the preset reference value the colors are determined not to be the same by the operation unit.

Additionally, according to an exemplary embodiment of the present invention, the reference value is 0.05 (5%).

Additionally, according to an exemplary embodiment of the present invention, the reference object is a coated color or uncoated color described in the Pantone book.

Additionally, according to an exemplary embodiment of the present invention, in determining whether the colors are the same or not by an operation unit, when the value of the mean deviation ratio is equal to or higher than the preset reference value the colors are determined not to be the same, a step of re-selecting the reference object is further comprised, after determining whether the colors are the same or not by an operation unit; and the step of emitting light to the reference object and to the measurement object, using a light source of the spectrophotometer, and reflecting the same is re-performed, thereby determining whether the colors are the same or not by the operation unit.

Additionally, according to an exemplary embodiment of the present invention, the light has a wavelength ranging from 400 nm to 800 nm.

Additionally, according to an exemplary embodiment of the present invention, the measurement object is a Cu—Sn alloy, a Cu—Zn alloy, Cu—Ni alloy, or a Cu—Si alloy.

Additionally, according to an exemplary embodiment of the present invention, the reference object is a sample whose wavelength-wise reflectance for each composition is measured using a spectrophotometer.

Additionally, according to an exemplary embodiment of the present invention, the reference object is a Cu—Sn alloy, a Cu—Zn alloy, Cu—Ni alloy, or a Cu—Si alloy.

Additionally, with respect to the alloy in which the colors are determined to be the same by the operation unit by the method for analyzing the color, the present invention provides an electronic recording medium, in which data including the information on the composition of the alloy, wavelength-wise reflectance of the alloy, and the color of the alloy are electronically recorded.

Additionally, the present invention provides an automated method for analyzing the color using a spectrophotometer, including: controlling the wavelength range of the light emitted from the light source of a spectrophotometer; inserting a reference object and a measurement object into a sample charging unit of the spectrophotometer and emitting light in a wavelength ranging from 400 nm to 800 nm; measuring the reflectance of light emitted by reflection from the light reference object and the measurement object inserted into the sample charging unit; calculating the absolute value of the difference between the measured wavelength-wise reflectance of the measurement object and of the reference object, as the deviation value, and calculating the average value thereof, in an operation unit; dividing the average value of the difference in reflectance measured in the wavelength range of the light by the reflectance value measured in the wavelength range of the light, thereby obtaining the mean deviation ratio of reflectance; and determining that the colors are the same when the mean deviation ratio is less than 0.05, thereby determining as the color of the measurement object with respect to the reflectance value measured in the wavelength range of the light.

Additionally, the present invention provides an automated system for analyzing a color using a spectrophotometer, which includes: a light source unit emitting the light in the region of visible light; a sample charging unit through which two lights emitted from the light source unit penetrate; a detection unit (detector) for measuring the reflectance of light emitted from a measurement object and a reference object which are charged into the sample charging unit; and an operation unit for comparing the reflectance of light measured in the detection unit and calculating the difference in reflectance with respect to the measurement object and the reference object.

Additionally, the present invention provides a method for designing an alloy using a spectrophotometer, which includes: charging a first alloy, which includes only color information of an alloy and a second alloy, which includes only composition information of the alloy into a sample charging unit of a spectrophotometer; emitting light into the first alloy and the second alloy using the light source of the spectrophotometer and reflecting the same; measuring the wavelength-wise reflectance while changing the wavelength of the light, which is directed from the light source to the first alloy and the second alloy, by a detection unit of the spectrophotometer; calculating the absolute value of the difference between the measured wavelength-wise reflectance of the first alloy and the second alloy, as the deviation value, and calculating the average value thereof, in an operation unit; dividing the average value by the wavelength-wise reflectance value of the reference object, thereby obtaining the mean deviation ratio of reflectance; and comparing the mean deviation ratio with 0.05, thereby determining whether the compositions of the first and second alloys are the same; wherein, with regard to the determining of whether the compositions of the first and second alloys are the same in the operation unit, when the mean deviation ratio is less than 0.05, the first and second alloys are determined to be the same, whereas when the mean deviation ratio is equal to or higher than 0.05, the first and second alloys are determined not to be the same, in the operation unit.

Additionally, the present invention is characterized in that, in determining whether the compositions of the first and second alloys are the same in the operation unit, when the mean deviation ratio is equal to or higher than 0.05, the first and second alloys are determined not to be the same, a step of re-selecting the second alloy as a third alloy by changing the second alloy is further comprised, after determining whether the first and second alloys are the same or not in an operation unit; and the step of emitting light the first and third alloys, using a light source of the spectrophotometer, and reflecting the same is re-performed, thereby determining whether the compositions are the same or not in the operation unit.

Additionally, the present invention provides a method for designing an alloy with a desired color, which includes: in an electronic operation device to which the electronic recording medium is inserted, selecting the color of an alloy among the data values recorded in the recording medium; and automatically matching the composition of an alloy corresponding to a desired color in the electronic operation device using the information on the composition of the alloy recorded in the recording medium, wavelength-wise reflectance, and a color data of the alloy, and indicating the same.

Additionally, the present invention provides an alloy designed using the method for designing an alloy with a desired color.

MODES FOR CARRYING OUT THE INVENTION

The advantages and features, and the invention to achieve the same will be clarified by referring to the exemplary embodiments described in detail herein below along with the accompanying drawings. However, the present invention should not be construed as limited to these exemplary embodiments set forth herein below but may be embodied in many different forms, and these exemplary embodiments are provided for illustrative purpose so that the disclosure of the present invention will be thorough and complete and defined as such to fully convey the scope of the present invention to those skilled in the art. In the drawings, the size and relative size of each layer and region may be exaggerated for clarity. The method for analyzing the color of a color alloy using reflectance will be explained herein below.

Example 1

In the method for analyzing the color of a color alloy according to the present invention, the color alloy to be quantitatively analyzed for the analysis of the color of the color alloy is called "a measurement object". The alloy to be a subject to be compared with the color of the color alloy is called "a reference object". The data including the color of the measurement object and the color of the reference object are placed on a measurement device using a spectrophotometer. The reference object may include data of pictures, etc., which includes not only the actual alloy but also the particular size including the color of an alloy.

In a photoelectric spectrophotometer for the measurement of the spectra of near ultraviolet light, visible light, and near infrared light regions, a detector such as a photoelectric tube, a photomultiplier, and a photoconductive device may be used. Meanwhile, in an infrared spectrophotometer which can measure the spectra ranging from near infrared to far infrared, a thermocouple, a voltmeter, a semi-conductor, etc., may be used.

In a passive-type spectrophotometer, transmittance or absorbance of a sample can be obtained by comparing the intensities of the transmitted light of a reference sample and a sample device for each wavelength, after inserting the device into an optical path by moving the device in a single beam type. In an automatic-type spectrophotometer, a double beam type is used in which the beam at one end is allowed to pass through a reference sample while the beam at the other end is allowed to pass through a sample device and the intensities of the transmitted beams at both ends are compared thereby obtaining absorbance or transmittance.

The action described above is continuously proceeded with respect to the wavelength and recorded automatically. The double beam type has two different forms. One type is that the light emitted from a light source is divided into two beams and induce them into a reference sample and a sample device, respectively, and the other type is that a single strand of beam is converted temporarily and is allowed to pass alternatingly to both devices. In a spectrophotometer used in the visible light and ultraviolet light regions, the second type of spectrophotometry is generally used.

In a method for analyzing the color of a color alloy according to an exemplary embodiment of the present invention, a spectrophotometer in a double beam type may be used.

In the method for analyzing the color of a color alloy, the measurement object and the reference object are charged into the charging unit of a spectrophotometer. Then, the wavelength-wise reflectivity is measured by emitting light to the charged measurement object and reference object and reflecting the light. In particular, since the measurement is made by the double beam type, the wavelength-wise reflectance can be obtained for two different samples.

Wavelength-wise reflectance may be obtained with regard to the quantitative data released from two different samples. The difference in the measured wavelength-wise reflectance between the measurement object and the reference object can be compared with the reflectance of the reference object.

The reflectance comparison between the measurement object and the reference object with respect to the difference in reflectance over the entire wavelength may be calculated by Equation 4 below.

Wavelength-wise reflectance comparison=|reflectance of a measurement object−reflectance of a reference object|/reflectance of a reference object    [Equation 4]

In Equation 4 above, the value of the wavelength-wise reflectance may be a mean deviation ratio of the reflectance obtained by calculating the absolute value of the difference between the measured wavelength-wise reflectance of the measurement object and of the reference object over the entire wavelength, as the deviation value, and calculating the average value thereof; and dividing the average value by the reflectance value of the reference object. The comparison value of the wavelength-wise reflectance may be a mean deviation ratio.

When the mean deviation ratio calculated by Equation 4 above is less than the reference value, the colors may be determined to be the same. By the same token, when the value of the mean deviation ratio is equal to or higher than the reference value, the colors may be determined to be different from each other. The reference value may be 0.05 (5%).

In the operation process described above, the calculation for the data with respect to the wavelength-wise reflectance may be carried out in an operation unit. The wavelength-wise reflectance may be the data for the reference object and measurement object measured in the measurement unit of a spectrophotometer.

In a method for analyzing the color using reflectance according to an exemplary embodiment of the present invention, when the colors are determined to be the same as a result of the operation as in the above measurement, the process of analyzing the color may be terminated.

Figure 2:
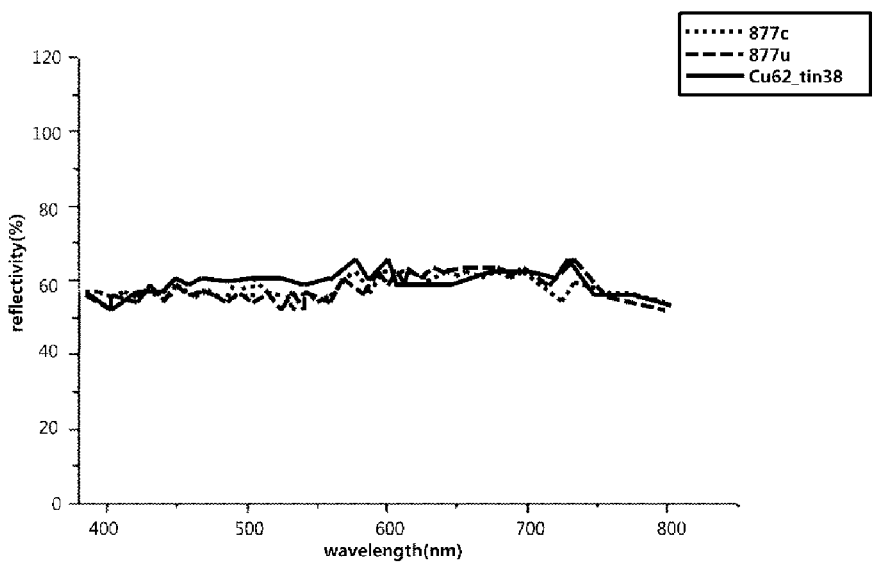
FIG. 2 shows a graph illustrating the measurement results of entire wavelength-wise reflectance according to an exemplary embodiment of the present invention.

FIG. 2 shows a graph illustrating the measurement results of wavelength-wise reflectance according to an exemplary embodiment of the present invention.

In FIG. 2, 877c represents a number of the Pantone book. As described above, c in the number of the Pantone book refers to a number for a coated sample. In FIG. 2, 877u refers to a number for an uncoated sample. In FIG. 2, Cu62_tin38 means that 62 wt % of Cu and 38 wt % of Sn.

In a method for analyzing the color using reflectance according to an exemplary embodiment of the present invention, as a reference sample, a coated color and uncoated color of the Pantone book may be used. The reference object may be a Cu—Sn alloy, a Cu—Zn alloy, a Cu—Ni alloy, or a Cu—Si alloy, and may be a sample for which the wavelength-wise reflectance for each composition was measured using the spectrophotometer.

Alternatively, an electronic recording medium in which the information on the composition and wavelength-wise reflectance of an alloy, and the color of the alloy are electronically recorded may be used.

In the graph of FIG. 2, the measurement result of the comparison values of the wavelength-wise reflectance with respect to 877c and Cu62_tin38 was shown to be less than 0.05. From these results, 877c and Cu62_tin38 may be determined to be the same color.

By the same token, 877u and Cu62_tin38 may be determined to be the same color.

From the graph of FIG. 2, 877c, 877u, and Cu62_tin38 may be determined to be the same color.

Example 2

The wavelength-wise reflectance can be measured with respect to a different color alloy in the same manner as in Example 1.

Figure 3:
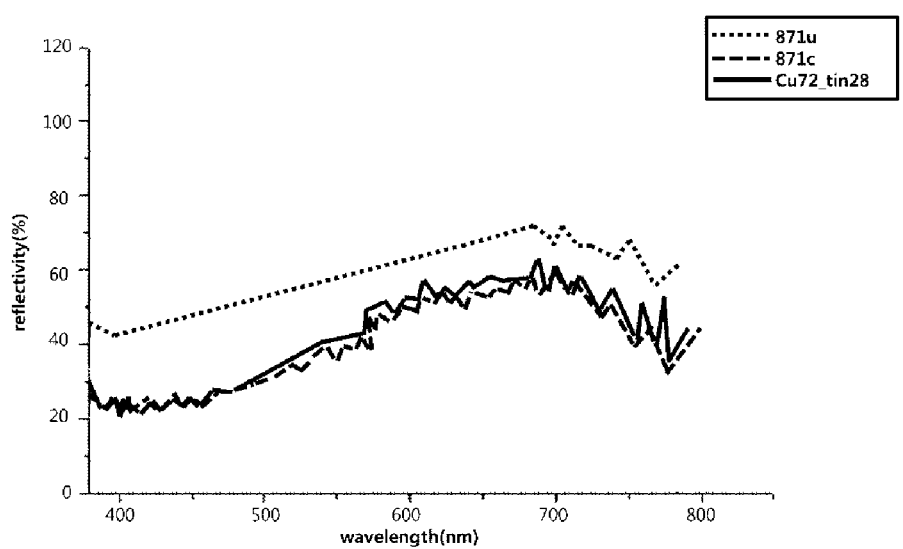
FIG. 3 shows a graph illustrating the measurement results of entire wavelength-wise reflectance according to another exemplary embodiment of the present invention.

FIG. 3 shows a graph illustrating the measurement results of wavelength-wise reflectance according to another exemplary embodiment of the present invention.

FIG. 3 shows the results of wavelength-wise reflectance measured using a spectrophotometer with respect to 871c and Cu72_tin28. The measurement process may be performed in the same manner as described in Example 1.

Referring to FIG. 3, when the mean deviation ratios for 871c and Cu72_tin28 were shown to be less than 0.05 and thus they may be determined to be the same color. However, the mean deviation ratios for 871u and Cu72_tin28 were shown to be equal to or higher than 0.05 and thus they may be determined not to be the same color.

As described in Examples 1 and 2, when the mean deviation ratio for the color according to the Pantone book index and for the color of a measurement object is shown to be less than 0.05, the process of analyzing a color alloy may be completed. However, when the mean deviation ratio is shown to be equal to or higher than 0.05, the measurement of wavelength-wise reflectance for the color according to the Pantone book index and for the color of a measurement object using a spectrophotometer may be re-performed. In particular, the re-measurement of the wavelength-wise reflectance may refer to a re-selection of a reference object, and re-performing the step of emitting the light of a light source of a spectrophotometer to the re-selected reference object and the measurement object and reflecting the same, and by proceeding as such, it is possible to determine whether the colors are the same in an operation unit. The wavelength-wise reflectance can be converted into % value by multiplying 100 thereto.

The samples that can be used as the measurement object may be a Cu—Sn alloy, a Cu—Zn alloy, a Cu—Ni alloy, or a Cu—Si alloy.

The color-wise composition according to the composition of an alloy can be obtained by the process described above.

An automated method for analyzing a color using a spectrophotometer may be drawn using the method for analyzing a color according to an alloy as described above. The automated method for analyzing the color using a spectrophotometer may include: controlling the wavelength range of the light emitted from the light source of a spectrophotometer; inserting a reference object and a measurement object into a sample charging unit of the spectrophotometer and emitting light in a wavelength ranging from 400 nm to 800 nm; measuring the reflectance of light emitted by reflection from the light reference object and the measurement object inserted into the sample charging unit; calculating the absolute value of the difference between the measured wavelength-wise reflectance of the measurement object and of the reference object, as the deviation value, and calculating the average value thereof, in an operation unit; dividing the average value of the difference in reflectance measured in the wavelength range of the light by the reflectance value measured in the wavelength range of the light, thereby obtaining the mean deviation ratio of reflectance; and determining that the colors are the same when the mean deviation ratio is less than 0.05, thereby determining as the color of the measurement object with respect to the reflectance value measured in the wavelength range of the light. The above process may be automatically performed after the process of introducing the measurement object into a charging unit.

Figure 4:
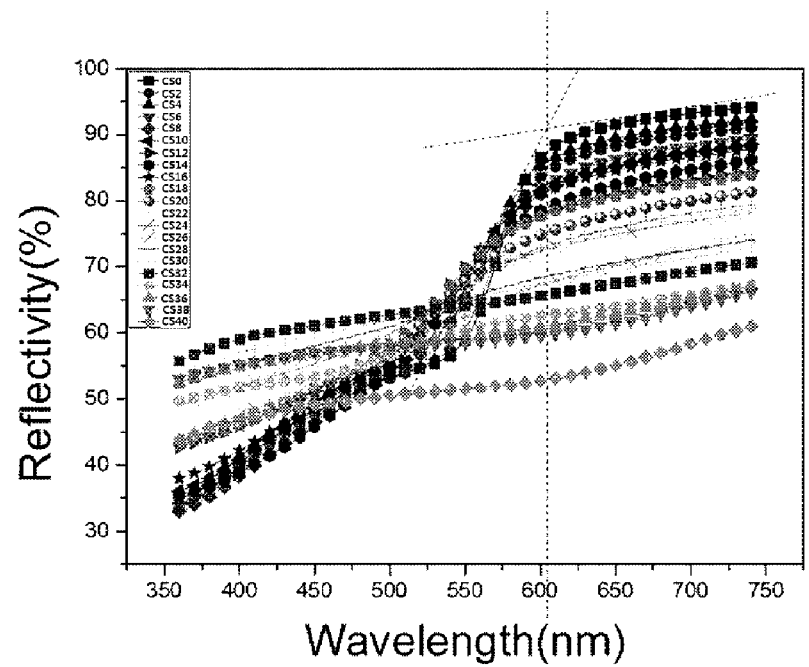
FIG. 4 shows a graph illustrating the measurement results of entire wavelength-wise reflectance according to the composition of an alloy according to an exemplary embodiment of the present invention.

FIG. 4 shows a graph illustrating the measurement results of wavelength-wise reflectance according to the composition of an alloy according to an exemplary embodiment of the present invention.

Referring to FIG. 4, it can be confirmed that CS0, CS2, CS4, . . . , CS40, etc., are recorded on the upper left end as an index. CS0 refers to 100 wt % of Cu and 0 wt % of Sn. By the same token, CS40 may refer to 60 wt % of Cu and 40 wt % of Sn. By going through such a process, the composition-wise reflectance with respect to the Cu—Sn alloy, Cu—Zn alloy, Cu—Ni alloy, or Cu—Si alloy may be obtained.

Additionally, by expanding the same further, with respect to the alloy determined to be the same color as a result of hue analysis for the coated color or uncoated color disclosed in the Pantone book, a recording medium for an electronic operation device possessing the database of an alloy, which possesses the information on composition and wavelength-wise reflectance within the visible light region and color information on the alloy, can be obtained. The color information of the alloy may be a color image complying with the required particular size.

The same color may be a color for the composition of an alloy, in which the value of the mean deviation ratio with respect to the alloy composition measured using a spectrophotometer and the coated color or uncoated color disclosed in the Pantone book is determined to be less than 5%.

The samples of alloys which came out of the database of the thus-obtained alloys can be used as a reference object according to Examples 1 and 2.

If color data and composition data according to a color alloy measured using a spectrophotometer are available as described above, a color for an alloy according to the consumers' request can be designed. The procedure of designing an alloy color will be described in detail herein below.

A method for designing an alloy using a spectrophotometer, including: charging a first alloy, which includes only color information of an alloy and a second alloy, which includes only composition information of the alloy into a sample charging unit of a spectrophotometer; emitting light into the first alloy and the second alloy using the light source of the spectrophotometer and reflecting the same; measuring the wavelength-wise reflectance while changing the wavelength of the light, which is directed from the light source to the first alloy and the second alloy, by a detection unit of the spectrophotometer; calculating the absolute value of the difference between the measured wavelength-wise reflectance of the first alloy and the second alloy, as the deviation value, and calculating the average value thereof, in an operation unit; dividing the average value by the wavelength-wise reflectance value of the reference object, thereby obtaining the mean deviation ratio of reflectance; and comparing the mean deviation ratio with 0.05, thereby determining whether the compositions of the first and second alloys are the same; wherein, with regard to the determining of whether the compositions of the first and second alloys are the same in the operation unit, when the mean deviation ratio is less than 0.05, the first and second alloys are determined to be the same, whereas when the mean deviation ratio is equal to or higher than 0.05, the first and second alloys may be determined not to be the same, in the operation unit.

In determining whether the compositions of the first and second alloys are the same in the operation unit, when the mean deviation ratio is equal to or higher than 0.05, the first and second alloys are determined not to be the same, a step of re-selecting the second alloy as a third alloy by changing the second alloy is further comprised, after determining whether the first and second alloys are the same or not in an operation unit; and the step of emitting light the first and third alloys, using a light source of the spectrophotometer, and reflecting the same may be re-performed and thereby whether the compositions are the same or not may be determined in the operation unit.

In addition, a method of designing an alloy with a desired color may further include, in an electronic operation device, in which an electronic recording medium which includes the composition, color, and wavelength-wise reflectance of an alloy is inserted, a step of selecting the color of an alloy among the data values recorded in the recording medium; and automatically matching the composition of an alloy corresponding to a desired color in the electronic operation device using the information on the composition of the alloy recorded in the recording medium, wavelength-wise reflectance, and a color data of the alloy, and indicating the same.

The first alloy which possesses the color information selected above may be a selected coated or uncoated color. If the quantitative data relating to the color according to alloy composition is available through the process described above, it may be possible to change the physical properties by changing the alloy composition according to the intended use thereof by analyzing the attributes of an alloy according to the composition.

Figure 5:
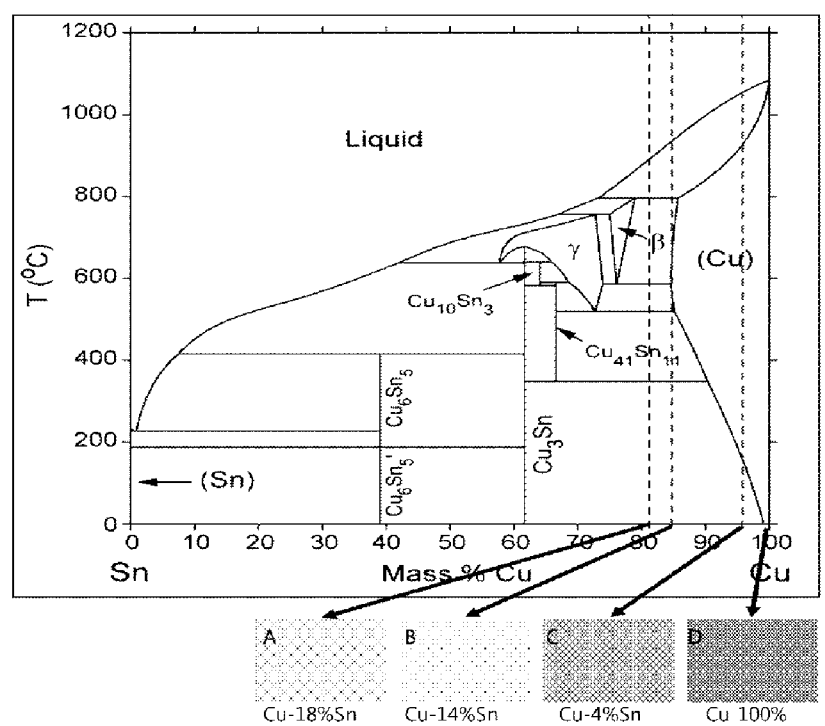
FIG. 5 shows a graph illustrating the colors of a composition-wise alloy according to the phase diagram according to an exemplary embodiment of the present invention.

FIG. 5 shows a graph illustrating the colors of a composition-wise alloy according to the phase diagram according to an exemplary embodiment of the present invention.

In FIG. 5, y axis may refer to temperature and x axis may refer to a composition ratio (mass ratio). In FIG. 5, D may represent a case where Cu is 100 wt %; C may represent a case where Cu is 96 wt % and Sn is 4 wt %; B may represent a case where Cu is 86 wt % and Sn is 14 wt %; and A may represent a case where Cu is 62 wt % and Sn is 38 wt %.

If a phase diagram according to a composition is available as shown in FIG. 5, it is possible to design an alloy according to color. As such, a designed alloy can be provided from the alloys, in which alloy information and color information are available, using a spectrophotometer.

An automated system for analyzing the color will be described in detail herein below.

Figure 6:
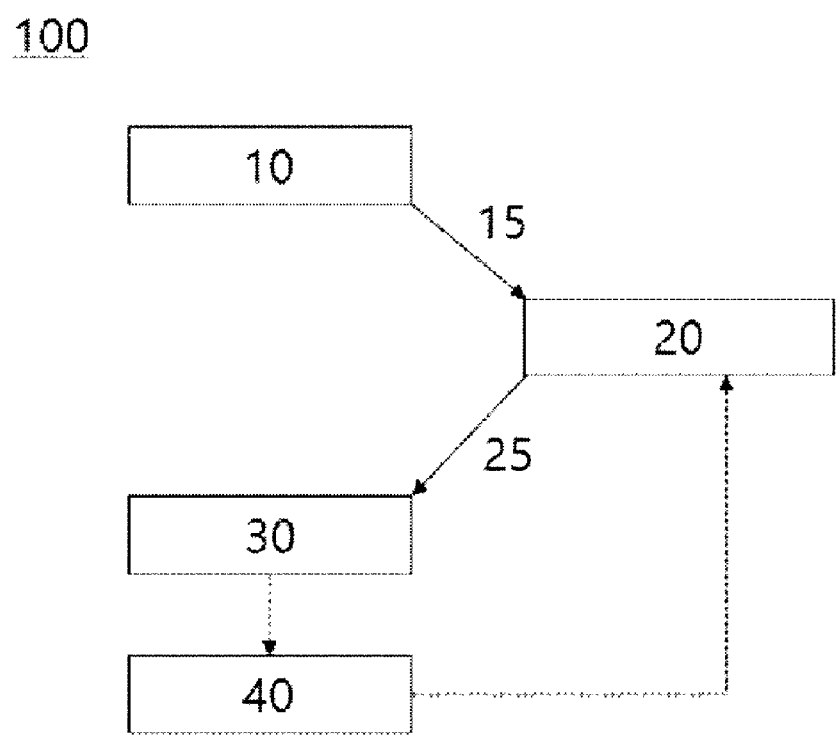
FIG. 6 shows a block diagram illustrating an automated system for analyzing colors using a spectrophotometer according to an exemplary embodiment of the present invention.

FIG. 6 shows a block diagram illustrating the feature of an automated system 100 for analyzing colors using a spectrophotometer according to an exemplary embodiment of the present invention.

Referring to FIG. 6, the automated system 100 for analyzing the color using the spectrophotometer may include a light source unit 10 emitting the light in the region of visible light; a sample charging unit 20 through which the incident light 15 emitted from the light source unit 10 penetrates; a detection unit 30 for measuring the reflectance of light 25 emitted by transmission (transmitted light) from the measurement object and the reference object which are charged into the sample charging unit 20; and an operation unit 40 for comparing the reflectance of light measured in the detection unit 30 and calculating the difference in reflectance with respect to the measurement object and the reference object. In the automated system 100 for analyzing the color using the spectrophotometer, when the comparison value (Equation 4) of the wavelength-wise reflectance for the measurement object and the reference object is shown to be equal to or higher than 0.05 in the operation unit 40, a signal can be sent to the sample charging unit 20 so as to change the reference object inserted into the sample charging unit 20.

If the comparison value of the wavelength-wise reflectance between the measurement object and the reference object is shown to be less than 0.05, a signal that the colors possessed by the measurement object and the reference object are the same can be sent to a sample charging unit 20 and thereby the measurement result can be indicated to a user.

Although the present invention has been explained in connection with the accompanying drawings, they are merely exemplary embodiments provided for illustrative purposes among various forms of embodiments including the gist of the present invention so that those skilled in the art can easily practice, and thus it is obvious that the present invention should not be limited to these exemplary embodiments explained above. Accordingly, the scope of the present invention should be interpreted by the appended claims below, and all the technical concepts which are within the equivalent scope of the present invention through modifications, substitutions, replacements, etc., may be included within the claim scope of the present invention unless they depart from the gist of the present invention. Furthermore, it should be understood that some of the features in drawings are exaggerated or reduced than their actual sizes, for more clearly explaining the technical features of the present invention.

DESCRIPTION OF REFERENCE NUMERALS

100: automated system for analyzing the color
10: light source unit
15: incident light
20: sample charging unit
25: transmitted light
30: detection unit
40: operation unit

What is claimed is:

1. A method for analyzing a color of a color alloy using reflectance, wherein the method comprises:
    charging a measurement object and a reference object into a sample charging unit of a spectrophotometer;
    emitting light to the reference object and to the measurement object, using a light source of the spectrophotometer, and reflecting the same;
    measuring wavelength-wise reflectance while changing a wavelength of the light, which is directed from the light source to the measurement object and to the reference object, by a detection unit of the spectrophotometer;
    calculating an absolute value of difference between wavelength-wise reflectance measured from the measurement object and from the reference object, as a deviation value, and calculating an average value thereof, in an operation unit;
    dividing the average value by the wavelength-wise reflectance of the reference object, thereby obtaining a mean deviation ratio of reflectance; and
    comparing the mean deviation ratio with a preset reference value, thereby determining whether the colors of the measurement object and the reference object are same or not by an operation unit,
    wherein, in determining whether the colors are same or not by an operation unit, when the value of the mean deviation ratio is less than the preset reference value the colors are determined to be same by the operation unit, whereas when the value of the mean deviation ratio is equal to or higher than the preset reference value the colors are determined not to be same by the operation unit.

2. The method of claim 1, wherein the preset reference value is 0.05.

3. The method of claim 1, wherein the reference object is a coated color or uncoated color described in the Pantone book.

4. The method of claim 1, wherein, in determining whether the colors are same or not by an operation unit, when the value of the mean deviation ratio is equal to or higher than the preset reference value the colors are determined not to be same, a step of re-selecting the reference object is further comprised, after determining whether the colors are same or not by an operation unit; and the step of emitting light to the reference object and to the measurement object, using a light source of the spectrophotometer, and reflecting the same is re-performed, thereby determining whether the colors are same or not by the operation unit.

5. The method of claim 1, wherein the light has a wavelength ranging from 400 nm to 800 nm.

6. The method of claim 1, wherein the measurement object is a Cu—Sn alloy, a Cu—Zn alloy, a Cu—Ni alloy, or a Cu—Si alloy.

7. The method of claim 1, wherein the reference object is a sample whose wavelength-wise reflectance for each composition is measured using a spectrophotometer.

8. The method of claim 7, wherein the reference object is a Cu—Sn alloy, a Cu—Zn alloy, a Cu—Ni alloy, or a Cu—Si alloy.

9. The method of claim 1 further comprising recording, on an electronic recording medium data comprising information on a composition of the alloy, wavelength-wise reflectance of the alloy, and the color of the alloy.

10. An automated method for analyzing a color using a spectrophotometer, comprising:
   controlling a wavelength range of a light emitted from a light source of the spectrophotometer;
   inserting a reference object and a measurement object into a sample charging unit of the spectrophotometer and emitting light in a wavelength ranging from 400 nm to 800 nm to the reference object and the measurement object;
   measuring reflectance of light emitted by reflection from the reference object and the measurement object inserted into the sample charging unit;
   calculating an absolute value of difference between wavelength-wise reflectance measured from the measurement object and from the reference object, as a deviation value, and calculating an average value thereof, in an operation unit;
   dividing the average value of the difference in reflectance measured in the wavelength range of the light by a reflectance value measured in the wavelength range of the light, thereby obtaining a mean deviation ratio of reflectance; and
   determining that the colors of the reference object and the measurement object are same when the mean deviation ratio is less than 0.05 and determining the color of the measurement object as a color of the reflectance value measured in the wavelength range of the light.

11. An automated system for analyzing a color using a spectrophotometer, comprising:
   a light source emitting light in a region of visible light;
   a sample charger charging a measurement object and a reference object therein, wherein two projection of light emitted from the light source are provided simultaneously to the measurement object and the reference object;
   a detector measuring reflectance of light emitted by transmission from the measurement object and the reference object which are charged into the sample charger; and
   an operator comparing the reflectance of light measured in the detector and calculating difference in reflectance between the measurement object and the reference object.

12. A method for designing an alloy using a spectrophotometer, comprising:
   charging a first alloy and a second alloy into a sample charging unit of a spectrophotometer;
   emitting light into the first alloy and the second alloy using a light source of the spectrophotometer and reflecting the same;
   measuring wavelength-wise reflectance while changing a wavelength of the light, which is directed from the light source to the first alloy and the second alloy, by a detection unit of the spectrophotometer;
   calculating an absolute value of difference between the wavelength-wise reflectance measured from the first alloy and from the second alloy, as a deviation value, and calculating an average value thereof, in an operation unit;
   dividing the average value by a wavelength-wise reflectance value of the reference object, thereby obtaining a mean deviation ratio of reflectance; and
   comparing the mean deviation ratio with 0.05, thereby determining whether compositions of the first and second alloys are same,
   wherein, in determining whether the compositions of the first and second alloys are same in the operation unit, when the mean deviation ratio is less than 0.05, the first and second alloys are determined to be same, whereas when the mean deviation ratio is equal to or higher than 0.05, the first and second alloys are determined to be different, in the operation unit.

13. The method of claim 12, wherein, in determining whether the compositions of the first and second alloys are same in the operation unit, when the mean deviation ratio is equal to or higher than 0.05, the first and second alloys are determined to be different, a step of re-selecting the second alloy as a third alloy is further comprised, after determining whether the compositions of the first and second alloys are same or not in an operation unit; and the step of emitting light to the first and third alloys, using a light source of the spectrophotometer, and reflecting the same is re-performed, thereby determining whether the compositions of the first and third alloys are same or not in the operation unit.

14. A method for designing an alloy with a desired color, comprising:
   reading, by an electronic operation device, data from an electronic recording medium, the data being stored according to the method of claim 9 and comprising information on a composition of the alloy, wavelength-wise reflectance of the alloy, and the color of the alloy;
   selecting, by a user, a desired color among the color of the alloy recorded in the recording medium; and
   matching, by the electronic operation device, the composition of the alloy corresponding to the desired color using the information on the composition of the alloy recorded in the recording medium, wavelength-wise reflectance, and the color data of the alloy; and indicating, by the electronic operation device, the same to the user.

15. An alloy designed according to the method of claim 14.

16. The automated system according to claim 11, wherein the operator:
   calculates an absolute value of difference between the reflectance of light measured from the measurement object and from the reference object, as a deviation value, and calculating an average value thereof;
   divides the average value by the reflectance of light of the reference object, thereby obtaining a mean deviation ratio of the reflectance of light; and
   compares the mean deviation ratio with a preset reference value, thereby determining whether the colors of the measurement object and the reference object are same or not.

17. The automated system according to claim 16, wherein, in determining whether the colors are same or not by the operator, when the value of the mean deviation ratio is less than the preset reference value the colors are determined to be same by the operation unit, whereas when the value of the mean deviation ratio is equal to or higher than the preset reference value the colors are determined not to be same by the operation unit.

* * * * *